(12) United States Patent
Dickenson

(10) Patent No.: US 7,015,392 B1
(45) Date of Patent: Mar. 21, 2006

(54) HIGH TORSIONAL DUCTILITY WIRE AND METHODS OF MAKING THE SAME

(75) Inventor: Roger Dickenson, Roanoke, VA (US)

(73) Assignee: Accellent, Inc., Salem, VA (US)

( * ) Notice: Subject to any disclaimer, the term of this patent is extended or adjusted under 35 U.S.C. 154(b) by 0 days.

(21) Appl. No.: 10/446,644

(22) Filed: May 28, 2003

(51) Int. Cl.
*H01B 7/34* (2006.01)

(52) U.S. Cl. ....................................... 174/36
(58) Field of Classification Search ................. 174/36, 174/128.1, 126.1, 128.2; 600/585, 191, 194; 428/600, 607, 608
See application file for complete search history.

(56) References Cited

U.S. PATENT DOCUMENTS

| | | | | |
|---|---|---|---|---|
| 4,737,392 A | * | 4/1988 | Dambre | 428/35.8 |
| 5,324,328 A | | 6/1994 | Li et al. | 607/129 |
| 5,477,864 A | * | 12/1995 | Davidson | 600/585 |
| 5,674,273 A | | 10/1997 | Helland | 607/122 |
| 5,679,470 A | * | 10/1997 | Mayer | 428/662 |
| 6,329,069 B1 | * | 12/2001 | Azizi et al. | 428/600 |
| 6,399,886 B1 | * | 6/2002 | Avellanet | 174/128.1 |

FOREIGN PATENT DOCUMENTS

WO WO 96/25969 * 8/1996

OTHER PUBLICATIONS

Magellan Industrial Trading Company, INC, Data Sheet of MP35N May 1985.*
Peter A. Altman et al.; *Rotary Bending Fatigue of Coils and Wires Used in Cardiac Lead Design*, J. Biomed. Mat. Res., vol. 43, Issue 1; 1998; pp. 21-37.
S. Asgari et al.; *The Secondary Hardening Phenomenon in Strain-Hardened MP35N Alloy;* Acta mater; vol. 46, No. 16, 1998; pp. 5795-5806.
Fort Wayne Metals; *DFT™ Wire*; http://www.fwmetals.com/spec_sheets/dft.htm; 2000; pp. 1-2.
Carpenter Specialty Alloys; *Alloy Data Carpenter MP35N* Alloy*; http://carpenter.idesinc.com/datasheet.asp?e=3&u=e; Oct. 18, 2000; pp. 1-5.
J. M. Meagher; *Stresses from Flexure in Composite Helical Implantable Leads*; J. Medical Engineering and Physics, vol. 19; Oct. 1997; pp. 668-673.

* cited by examiner

*Primary Examiner*—William H. Mayo, III
(74) *Attorney, Agent, or Firm*—Timothy M. Honeycutt

(57) ABSTRACT

Various wires and methods of making the same are disclosed. In one aspect, a wire is provided that includes a core and a tube around the core. The tube is composed of an alloy containing about 33 to 37% nickel, about 31.5 to 39% cobalt, about 9 to 10.5% molybdenum, and about 19 to 21% chromium. The wire has an ultimate tensile strength of about 150 to 250 kpsi, an amount of cold work following a final anneal and a torsional ductility of greater than about 6 turns-to-failure per inch of the wire.

17 Claims, 6 Drawing Sheets

HIGH TORSIONAL DUCTILITY WIRE AND METHODS OF MAKING THE SAME

BACKGROUND OF THE INVENTION

1. Field of the Invention

This invention relates generally to metals processing, and more particularly to wires and methods of making the same.

2. Description of the Related Art

MP35N wires and MP35N-clad-silver wires are used in myriad of applications in industry. One of the most common uses of such wires is in the medical devices area. MP35N has been a material of choice for many years for lead wires in cardiac pacing devices, cardiac rhythm management devices, implantable defibrillators, neuro-stimulation devices, and other similar devices. These wires carry the electrical current from the pulse generator to the electrodes. They are typically either coiled or twisted into cables to produce a highly flexible, fatigue-resistant structure. They are also commonly coated with a polymer for electrical insulation either before or after coiling or cabling.

The wire for these medical devices should exhibit biocompatibility and be very tough and fatigue resistant. Historically, toughness has been specified only by requiring a certain tensile elongation in the final wire.

As with most metal wire production, conventionally produced MP35N clad silver wire goes through a series of cold draws with anneals interspersed. The cold draws bring the wire to a desired outer diameter and tensile strength. The anneals serve the purpose of softening the metal to allow further cold reduction. The amount of cold work and the annealing parameters (time and temperature) are tailored to obtain the final desired strength and perhaps other properties. For MP35N clad silver wire, the annealing temperature is typically around 1700° F. which is below the approximate 1761° F. melting point of silver, and well below the 1900 to 2000° F. temperature range at which MP35N is typically annealed. A final anneal is usually performed before a short series of final draws. The final anneal in conventional processing is short, on the order of twenty seconds or less. Such short anneals can provide the wire with relatively high final ultimate tensile strength and sufficient ductility to undergo the final draws.

A difficulty associated with conventionally produced MP35N clad silver wire is the potential for relatively low torsional strength. The problem stems from the fact that wire designers and consumers place great emphasis on ultimate tensile strength. Reliance on ultimate tensile strength as a measure of wire behavior is not necessarily counterintuitive. Knowledge of ultimate tensile strength provides a familiar measure of a material's ability to withstand commonly applied stresses, such as shear, bending, tension and compression. However, for structures subjected to torsion, such as coiled wires in a medical device lead, ultimate tensile strength alone may not be enough to predict the behavior of the wire.

The present invention is directed to overcoming or reducing the effects of one or more of the foregoing disadvantages.

SUMMARY OF THE INVENTION

In accordance with one aspect of the present invention, a wire is provided that includes a core and a tube around the core. The tube is composed of an alloy containing about 33 to 37% nickel, about 31.5 to 39% cobalt, about 9 to 10.5% molybdenum, and about 19 to 21% chromium. The wire has an ultimate tensile strength of about 150 to 250 kpsi, an amount of cold work following a final anneal and a torsional ductility of greater than about 6 turns-to-failure per inch of the wire.

In accordance with another aspect of the present invention, a method of processing is provided that includes imparting a first amount of cold work to a wire having a core and a tube around the core and annealing the wire at a temperature near but not over the melting point of the core for at least 30 seconds and sufficiently long thereafter to provide the wire with a torsional ductility of greater than about 6 turns-to-failure per inch of the wire. A second amount of cold work is imparted to the wire after annealing to provide the wire with a desire strength level.

In accordance with another aspect of the present invention, a method of processing is provided that includes imparting a first amount of cold work to a wire having a core and a tube around the core. The tube is composed of an alloy containing about 33 to 37% nickel, about 31.5 to 39% cobalt, about 9 to 10.5% molybdenum, and about 19 to 21% chromium. The wire is annealed at a temperature near but not over the melting point of the core for at least 30 seconds and sufficiently long thereafter to provide the wire with a torsional ductility of greater than about 6 turns-to-failure per inch of the wire. A second amount of cold work is imparted to the wire after annealing to give the wire a desired strength level.

In accordance with another aspect of the present invention, a wire is provided that includes a core and a tube around the core. The tube is composed of MP35N. The wire has has an ultimate tensile strength of about 150 to 250 kpsi, an amount of cold work following final anneal and a torsional ductility greater than about 6 turns-to-failure per inch of the wire.

In accordance with another aspect of the present invention, a wire is provided that includes a strand of alloy containing about 33 to 37% nickel, about 31.5 to 39% cobalt, about 9 to 10.5% molybdenum, and about 19 to 21% chromium. The strand has an ultimate tensile strength of about 150 to 250 kpsi, an amount of cold work following final anneal and a torsional of ductility greater than about 6 turns-to-failure per inch of strand.

In accordance with another aspect of the present invention, an electrical lead for a medical device is provided that includes an electrode, an insulating sleeve coupled to the electrode, and a wire coupled to the electrode and at least partially positioned in the insulating sleeve. The wire has a core and a tube around the core. The tube is composed of an alloy containing about 33 to 37% nickel, about 31.5 to 39% cobalt, about 9 to 10.5% molybdenum, and about 19 to 21% chromium. The wire has an ultimate tensile strength of about 150 to 250 kpsi, an amount of cold work following a final anneal and a torsional ductility of greater than about 6 turns-to-failure per inch of the wire.

BRIEF DESCRIPTION OF THE DRAWINGS

The foregoing and other advantages of the invention will become apparent upon reading the following detailed description and upon reference to the drawings in which.

DETAILED DESCRIPTION OF SPECIFIC EMBODIMENTS

Figure 1:
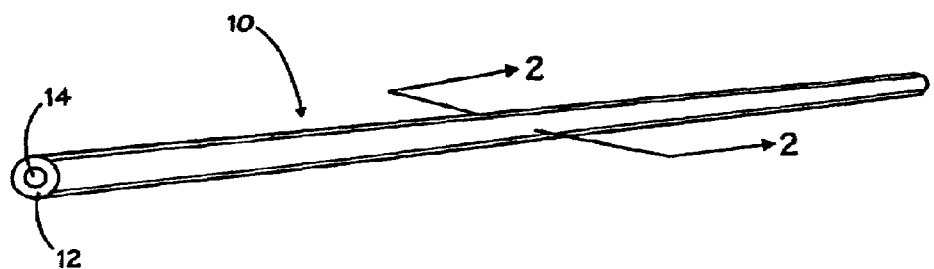
FIG. 1 is a pictorial view of an exemplary embodiment of a wire fabricated in accordance with the present invention.
Figure 2:
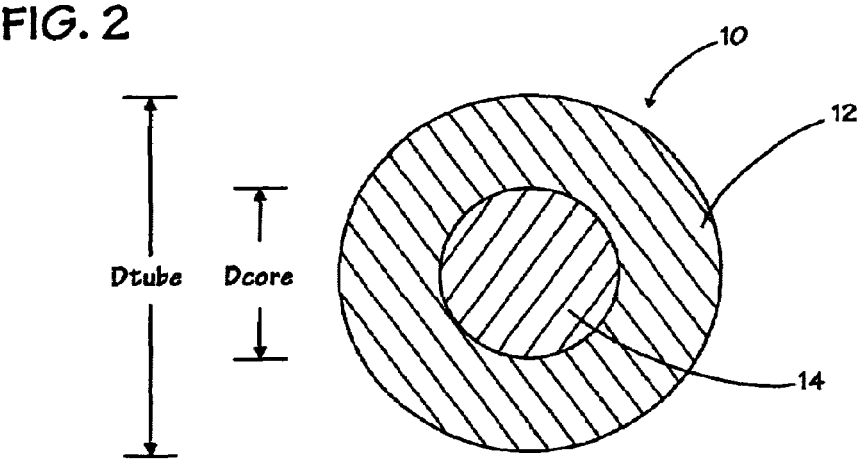
FIG. 2 is a cross-sectional view of FIG. 1 taken at section 2—2 in accordance with the present invention.

In the drawings described below, reference numerals are generally repeated where identical elements appear in more than one figure. Turning now to the drawings, and in particular to FIG. 1, therein is shown a pictorial view of an exemplary embodiment of a wire 10 fabricated in accordance with the present invention. The wire 10 is depicted as a relatively straight segment for simplicity of illustration. However, the skilled artisan will appreciate that wire 10 may be bent or otherwise deformed into any number of shapes. In this illustrative embodiment, the wire 10 is of a clad configuration in that it includes a tube 12 that surrounds a central core 14. With a clad configuration, the tube 12 can be composed of materials that exhibit desirable mechanical strength and corrosion resistance properties while the core 14 can be composed of materials that exhibit higher electrical conductivity than the tube material. As depicted in FIG. 2, which is a cross-sectional view of FIG. 1 taken at section 2—2, the diameter of the tube 12 $D_{tube}$ and the diameter of the core 14 $D_{core}$ may be selected such that the cross-sectional area of the core 14 makes up a certain percentage of the combined cross-sectional areas of the tube 12 and the core 14. In many applications, the core 14 may make up about 10 to 45% of the total cross-sectional area.

The tube 12 may be composed of a variety of materials that exhibit good mechanical strength properties and corrosion resistance. For example, alloys containing about 33 to 37% nickel, about 31.5 to 39% cobalt, about 9 to 10.5% molybdenum, and about 19 to 21% chromium may be used. One example of such alloys is MP35N. Other materials, such as Elgiloy, L605, Inconel, austenitic stainless steels or the like may be selected. These types of alloys exhibit many similarities in mechanical properties. The core 14 may be composed of a variety of materials exhibiting desirable electrical conductor properties, such as silver, gold, tantalum, copper, alloys of these or the like.

Figure 3:
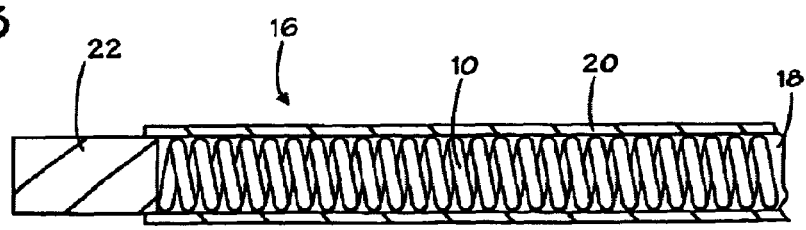
FIG. 3 is a cross-sectional view of an exemplary embodiment of a medical device electrical lead in accordance with the present invention.

The wire 10 may be used in a variety of applications. For example, and as depicted in FIG. 3, the wire 10 may be used in a lead 16 for use with a stimulator device, such as, for example, a cardiac stimulator or neuro-stimulator (not shown). The wire 10 is coiled and fitted within a lumen 18 of an external insulating sleeve 20. The wire 10 is in ohmic contact with an electrode 22 that is secured to one end of the sleeve 20. The electrode 22 is designed to make physical contact with a body tissue, such as a muscle or nerve.

It is desirable for the wire 10 to exhibit a certain level of torsional ductility so that the wire 10 will perform well in circumstances where torsional loads are imparted thereon. For example, if the wire 10 is coiled and used in the lead 16 depicted in FIG. 3, the act of coiling the wire 10 itself will impart a certain level of torsional loading thereon. Furthermore, whenever the lead 16 is flexed or otherwise bent, that bending will impart certain torsional loading upon some or all of the coils of the wire 10.

Figure 4:
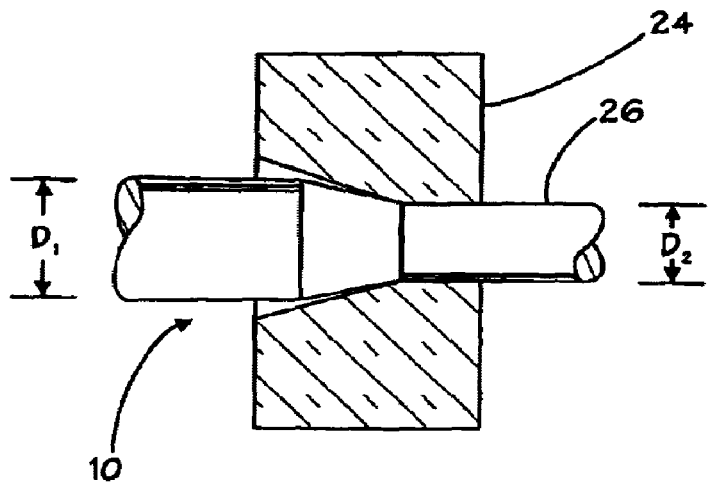
FIG. 4 is a side view of an embodiment of the wire of FIG. 1 positioned in a drawing die in accordance with the present invention.

An exemplary process flow for fabricating the wire 10 in accordance with the present invention will now be described in conjunction with FIGS. 2, 4 and 5. The process will be described in the context of an MP35N silver clad wire. Initially, samples of the tube 12 and the core 14 are selected with respective diameters $D_{tube}$ and $D_{core}$ that will result in a clad wire with a selected percentage of silver by cross-sectional area. The MP35N tube 12 is fully annealed at about 1900 to 2000° F. for a time to produce a fully recrystallized structure. Following the anneal, the tube 12 is drawn over the silver core 14.

If it is desired to change the physical and mechanical properties of the wire 10, a series of drawing and annealing processes may be performed. The drawing processes may be performed, for example, by drawing the wire 10 through a stationary draw die 24 depicted cross-sectionally in FIG. 4. Although the drawing process is compressive in nature, the drawing is actually accomplished by applying an axial load on the deformed end 26 of the wire 10. Note how the drawing process reduces the initial diameter $D_1$ of the wire 10 to a new post drawn diameter $D_2$. The deformed diameter $D_2$ closely approximates the size of the die 24. The drawing of the wire 10 through the die 24 imparts cold work to the wire 10. Thereafter, one or more anneals may be performed to release some of the cold work. The schedule of draws and anneals is selected so that the wire 10 will ultimately have a desired combination of ultimate tensile strength, percentage cold work, and wire size.

The annealing temperature is such that the temperature of the wire 10 does not exceed the melting point of the core 14. Silver melts at about 1761° F., so this represents the maximum temperature to which the wire 10 containing silver may be raised. Alternatively, if the core 14 is composed of gold, the maximum temperature will be 1945° F., and if the wire contains copper the maximum wire temperature will be 1981° F. Since the melting point of silver is well below the typical annealing temperature for MP35N (1900 to 2000° F.), it is advantageous to anneal the wire 10 as close to 1761° F. as feasible without exceeding it. MP35N will soften to some degree below the typical annealing range, but as the temperature is reduced, the duration must increase, and the ultimate degree of softening decreases. This restriction is less applicable to the potential core materials with melting points within or above the typical annealing range for MP35N.

The duration of other than the last anneal to be described in more detail below will typically be the minimum time required to soften the material sufficiently to allow subsequent cold drawing to be carried out successfully. These durations may vary according to wire size, with larger wire typically being annealed for longer times than smaller wire.

The anneals may be carried out in an inert atmosphere, such as argon, helium or the like. Optionally, a reducing atmosphere of hydrogen or hydrogen-argon mixtures may be used. Vacuum conditions may also be used. The equipment used for annealing typically varies with wire size. Larger wires may be annealed in a belt conveyor furnace, a pusher furnace, or a bell furnace. Below a certain size, the wire 10 may be annealed spool-to-spool in a strand furnace. In a strand furnace, the wire is passed through a "hot zone" at a prescribed speed. The anneal duration is determined by dividing the length of the "hot zone" by the wire speed.

An exemplary reduction/anneal schedule in accordance with the present invention is presented in Table 1 below. The second column indicates the pass, that is, a particular drawing step. The first column includes information regarding an anneal performed at a particular pass or more particular information regarding the drawing process. For example, the term "belt" refers to an anneal performed in a conveyor belt furnace at about 1650° F. in hydrogen and argon atmosphere for a duration of about 20 minutes. Similarly, the term "bell" refers to an anneal performed in a batch retort or bell furnace at about 1700° F. in hydrogen and argon atmosphere for a duration of 90 minutes. Finally, the term "strand" refers to a spool-to-spool type anneal process in a strand furnace at about 1730° F. in a hydrogen and argon atmosphere for a duration of 30 seconds. The term "BBII" refers to a bull block two die wire drawing machine. The term "MS" refers to multi-strand drawing machine.

The beginning wire diameter is 0.30200 inch. The target diameter for the wire 10 at final anneal using the reduction schedule set forth in Table 1 is about 0.00704 inches. The target final diameter is 0.005 inches. The target ultimate tensile strength is about 200 kpsi, but an advantageous range is about 150 to 250 kpsi. The target ultimate tensile strength is for the combination of the core 14 and the tube 12.

TABLE 1

REDUCTION SCHEDULE

| Pass | Die size (inches) | Reduction in cross-sectional area | Length (ft) | Elongation | Outer diameter reduction | Comments |
|---|---|---|---|---|---|---|
| 1 | 0.30200 | 0.368 | 16 | 1.583 | 0.205 | clad/anneal (belt) draw |
| 2 | 0.26100 | 0.253 | 21 | 1.339 | 0.136 | anneal (belt) sink |
| 3 | 0.22500 | 0.257 | 29 | 1.346 | 0.138 | anneal (bell) |
| 4 | 0.20000 | 0.210 | 36 | 1.266 | 0.111 | anneal (bell) |
| 5 | 0.17780 | 0.210 | 46 | 1.265 | 0.111 | anneal (bell) |
| 6 | 0.15800 | 0.210 | 58 | 1.266 | 0.111 | |
| 7 | 0.14060 | 0.208 | 73 | 1.263 | 0.110 | |
| 8 | 0.12515 | 0.208 | 92 | 1.262 | 0.110 | two die pass on bbii |
| 9 | 0.11135 | 0.208 | 116 | 1.263 | 0.110 | anneal (bell) |
| 10 | 0.09910 | 0.208 | 147 | 1.263 | 0.110 | begin "multi-die" passes |
| 11 | 0.08820 | 0.208 | 186 | 1.262 | 0.110 | |
| 12 | 0.07850 | 0.208 | 234 | 1.262 | 0.110 | |
| 13 | 0.06985 | 0.208 | 296 | 1.263 | 0.110 | anneal (strand) |
| 14 | 0.06218 | 0.208 | 373 | 1.262 | 0.110 | |
| 15 | 0.05525 | 0.210 | 473 | 1.267 | 0.111 | |
| 16 | 0.04910 | 0.210 | 599 | 1.266 | 0.111 | |
| 17 | 0.04365 | 0.210 | 758 | 1.265 | 0.111 | anneal (strand) |
| 18 | 0.03879 | 0.210 | 960 | 1.266 | 0.111 | |
| 19 | 0.03448 | 0.210 | 1,215 | 1.266 | 0.111 | |
| 20 | 0.03065 | 0.210 | 1,537 | 1.266 | 0.111 | |
| 21 | 0.02724 | 0.210 | 1,946 | 1.266 | 0.111 | |
| 22 | 0.02421 | 0.210 | 2,464 | 1.266 | 0.111 | anneal (strand) |
| 23 | 0.023000 | 0.097 | 2,730 | 1.108 | 0.050 | M5 |
| 24 | 0.021100 | 0.158 | 3,243 | 1.188 | 0.083 | |
| 25 | 0.019350 | 0.159 | 3,857 | 1.189 | 0.083 | |
| 26 | 0.017750 | 0.159 | 4,583 | 1.188 | 0.083 | |
| 27 | 0.016270 | 0.160 | 5,455 | 1.190 | 0.083 | |
| 28 | 0.015180 | 0.130 | 6,266 | 1.149 | 0.067 | |
| 29 | 0.014150 | 0.131 | 7,212 | 1.151 | 0.068 | |
| 30 | 0.013200 | 0.130 | 8,287 | 1.149 | 0.067 | |
| 31 | 0.012310 | 0.130 | 9,529 | 1.150 | 0.067 | |
| 32 | 0.011470 | 0.132 | 10,976 | 1.152 | 0.068 | |
| 33 | 0.010700 | 0.130 | 12,612 | 1.149 | 0.067 | |
| 34 | 0.009980 | 0.130 | 14,498 | 1.149 | 0.067 | |
| 35 | 0.009300 | 0.132 | 16,696 | 1.152 | 0.068 | |
| 36 | 0.008680 | 0.129 | 19,166 | 1.148 | 0.067 | |
| 37 | 0.008090 | 0.131 | 22,063 | 1.151 | 0.068 | |
| 38 | 0.007540 | 0.131 | 25,399 | 1.151 | 0.068 | |
| 39 | 0.007040 | 0.128 | 29,135 | 1.147 | 0.066 | final anneal M5 |
| 40 | 0.006560 | 0.132 | 33,555 | 1.152 | 0.068 | |
| 41 | 0.006120 | 0.130 | 38,554 | 1.149 | 0.067 | |
| 42 | 0.005710 | 0.129 | 44,289 | 1.149 | 0.067 | |
| 43 | 0.005000 | 0.233 | 57,760 | 1.304 | 0.124 | |

As noted above in the Background section, the final anneal in conventional wire drawing processes is typically performed for a relatively short duration, perhaps 10–20 seconds. Subsequent strength testing of wire drawn in such a fashion will likely reveal a desirable ultimate tensile strength. However, the conventional wire may exhibit relatively poor torsional ductility and thus be prone to torsion failure.

A discovery in accordance with the present invention is that torsional ductility is a characteristic that can be managed somewhat independently of tensile properties. In other words, increasing the duration of the final anneal, called out in Table 1 at pass number 39, to between about 30 and 180 seconds provides dramatic and unexpected improvement in the torsional ductility of the wire 10 without significantly reducing ultimate tensile strength. As used herein, "torsional ductility" is defined as the number of turns that may be imparted on a wire until the wire fails.

Figure 5:
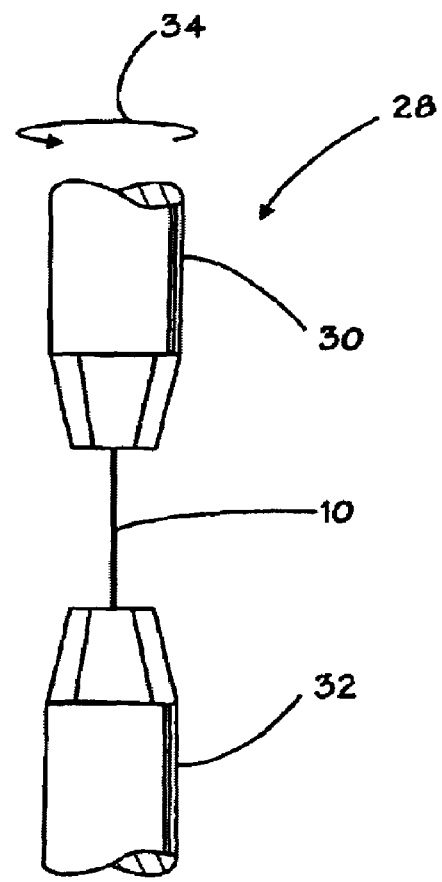
FIG. 5 is a schematic view of a torsion tester and an exemplary embodiment of the wire of FIG. 1 held therein.

To investigate the effects of final anneal duration on the torsional ductility of the wire 10, samples of the wire 10 given final anneals for various time periods and temperatures were placed in a torsion tester 28, which is represented schematically in FIG. 5. The wire 10 is secured between two chucks 30 and 32 with very little tension and the chuck 30 is rotated to twist the wire 10 as indicated by the arrow 34. The number of turns of the chuck 30 through 360° until the wire 10 fails is counted. The turns-to-failure represents a repeatable and easily understood measure of the torsional ductility of the wire 10. It is believed that there will be some dependence of the number of turns to failure on the length of the wire 10 that is placed in the torsion tester 28.

Therefore, it is possible to characterize the torsional ductility of the wire 10 in terms of the number of turns to failure per inch of wire. In the various experiments performed, a sample length of 1⅝ inches was used. So for a 1⅝ inch long sample that failed after 58 turns, the torsional ductility can be represented as 58 turns-to-failure/1⅝ inch or 35.7 turns-to-failure/inch of wire.

Samples of the wire 10 reduced according to the schedule set forth in Table 1 but with varying final anneal temperature, duration and post-final anneal cold working. The various samples were subjected to torsion test to determine any relationships between turns-to-failure, ultimate tensile strength, yield strength, percentage cold work and anneal duration. The results of those tests are set forth in Table 2 below. The value for the turns-to-failure is an average of between two and seven tested samples at a given diameter and cold work percentage. The description provides information related to the final anneal conditions and the type of subsequent cold work. The term "mini-bb" refers to a single die wire drawing machine used to perform the draws for the trials. The first trial run consisted of two samples that were subjected to typical conventional final anneal and cold work conditions. The remainder of Table 2 shows the results for trial runs 2–5, which were performed at different final anneal and post-final anneal cold work conditions.

TABLE 2

| Trial Run | Wire Diameter | % Cold Work | Turns-to-Failure (averaged over two to seven samples) | Yield Strength (kpsi) | Ultimate Tensile Strength (kpsi) | Elongation (%) | Description |
|---|---|---|---|---|---|---|---|
| 1st | 0.00628 | 93% | 7.5 | 205.6 | 251.9 | 4.0 | as-drawn--no final anneal |
|  | 0.00628 | 0% | 80 | 120.5 | 142.1 | 19.7 | 1700° F., 480 inch/min. (72 inch hot zone) |
| 2nd | 0.00628 | 0% | 135 | 98.3 | 136.7 | 24.0 | 1700° F., 30 ipm (36 inch hot zone) |
|  | 0.0553 | 22% | 9 | 152.9 | 183.1 | 3.3 | drawn 1 pass, mini-bb |
|  | 0.00496 | 38% | 7 | 176.1 | 204.9 | 2.8 | drawn 2 passes, mini-bb |
| 3rd | 0.00628 | 0% | 229 | 90.4 | 132.9 | 25.9 | 1700° F., 12 inch/min. (36 inch hot zone) |
|  | 0.0553 | 22% | 124 | 150.4 | 179.2 | 3.2 | drawn 1 pass, mini-bb |
|  | 0.00496 | 38% | 7 | 174.9 | 205.2 | 2.7 | drawn 2 passes, mini-bb |
| 4th | 0.00616 | 0% | 256 | 73.3 | 130.1 | 30.0 | 1730° F., 24 inch/min. (72 inch hot zone) |
|  | 0.00571 | 14% | 274 | 135.0 | 157.5 | 9.1 | drawn 1 pass, mini-bb |
|  | 0.00559 | 18% | 247 | 139.3 | 165.9 | 4.5 | drawn 1 pass, mini-bb |
|  | 0.00531 | 26% | 181 | 164.6 | 185.6 | 2.6 | drawn 1 pass, mini-bb |
|  | 0.00508 | 32% | 155 | 177.2 | 197.6 | 2.4 | drawn 1 pass, mini-bb |
|  | 0.00485 | 38% | 131 | 183.7 | 205.3 | 2.4 | drawn 1 pass, mini-bb |
|  | 0.00485 | 38% | 33 | 171.6 | 208.2 | 2.7 | drawn 2 passes (the first passed reduced diameter to 0.0053 |
| 5th | 0.00623 | 0% | 182.0 | 91.8 | 136.6 | 25.8 | 1730° F., 120 inch/min. (72 inch hot zone) |
|  | 0.00571 | 16% | 135.7 | 139.1 | 168.8 | 4.2 | drawn 1 pass, mini-bb |
|  | 0.00559 | 20% | 73.0 | 142.7 | 176.7 | 3.5 | drawn 1 pass, mini-bb |
|  | 0.00531 | 28% | 8.3 | 168.3 | 191.7 | 2.5 | drawn 1 pass, mini-bb |
|  | 0.00508 | 34% | 5.3 | 176.8 | 202.5 | 2.5 | drawn 1 pass, mini-bb |
|  | 0.00485 | 40% | 6.1 | 190.4 | 209.1 | 2.4 | drawn 1 pass, mini-bb |

The final anneal duration for trial run #2 is given by dividing the length of the hot zone by the wire travel speed. So for trial run #2, the final anneal duration is given by 36 inches divided by 30 inches/min. This translates into an anneal duration of 1.2 minutes or 72 seconds. The anneal durations for trial runs 3, 4 and 5 were 180 seconds, 180 seconds and 36 seconds respectively.

Figure 6:
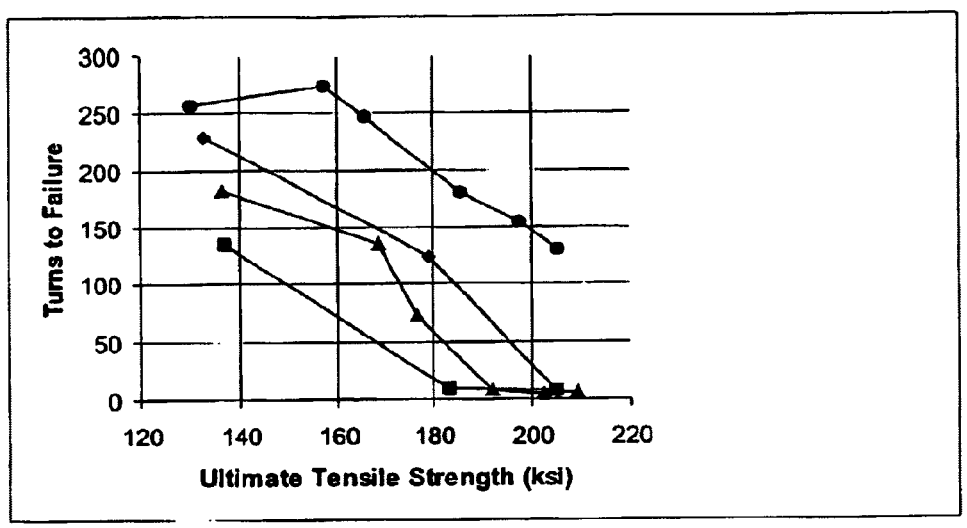
FIG. 6 is a chart of turns-to-failure versus ultimate tensile strength for an exemplary wire fabricated in accordance with the present invention.
Figure 7:
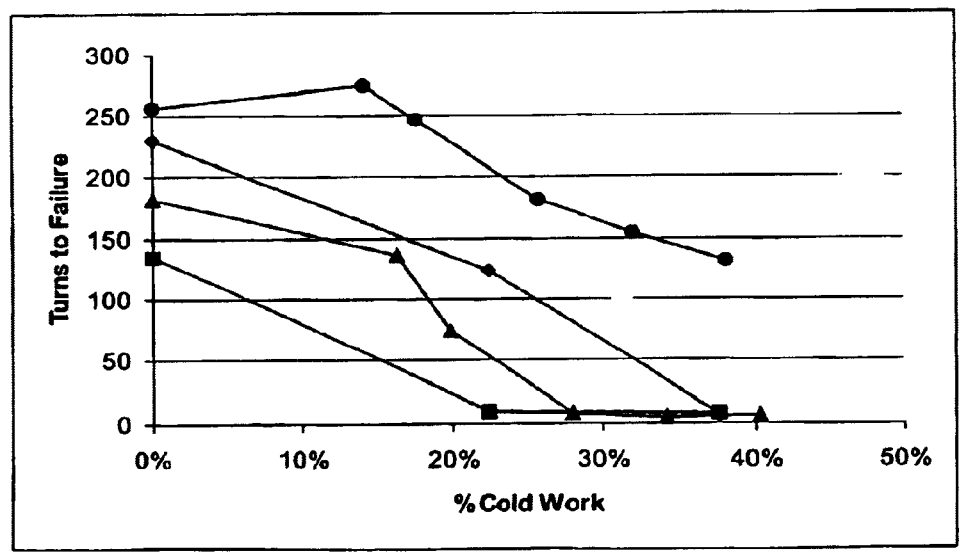
FIG. 7 is a chart of turns-to-failure versus cold work % for an exemplary wire fabricated in accordance with the present invention.
Figure 8:
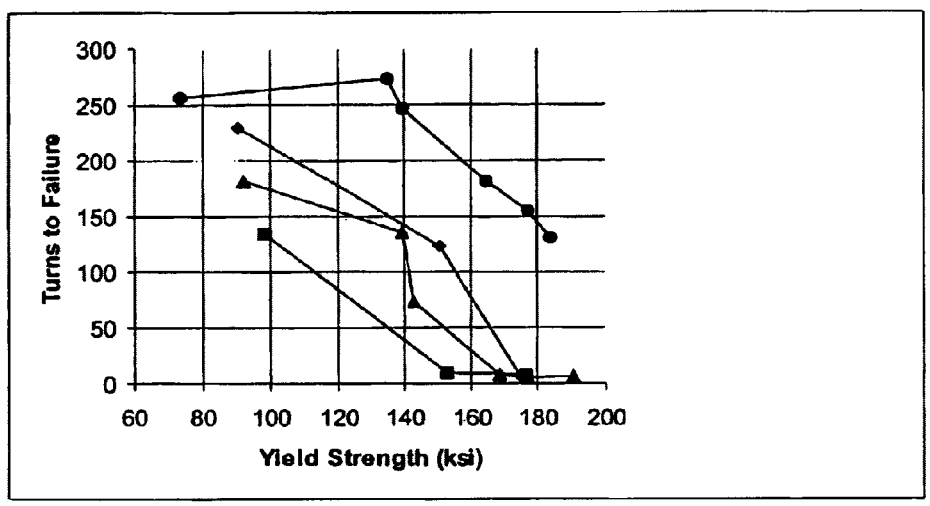
FIG. 8 is a chart of turns-to-failure versus cold yield strength for an exemplary wire fabricated in accordance with the present invention.
Figure 9:
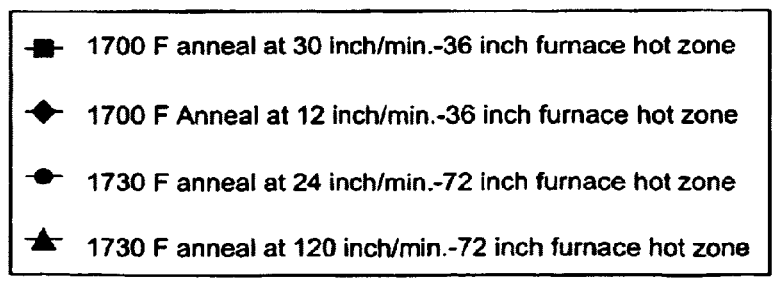
FIG. 9 is a legend for symbols used in FIGS. 6, 7 and 8.

FIGS. 6, 7 and 8 respectively depict plots of turns-to-failure versus ultimate tensile strength, turns-to-failure versus percentage cold work and turns-to-failure versus yield strength taken from the data pertaining to trials runs 2–5 in Table 2. FIG. 9 provides a legend to distinguish between the four curves depicted on each of the plots in FIGS. 6, 7 and 8. The results for trial run #2 are represented by the curves with square dots. Trial runs 3, 4 and 5 are represented respectively by the curves using diamonds, circles and triangles. As is evident from the plots in FIGS. 6, 7 and 8, a dramatic and very unexpected improvement in torsional ductility as represented by turns-to-failure may be realized by tailoring the duration of the final anneal of the wire. As noted above, the turns-to-failure may be divided by sample length to obtain normalized results. So a useful range may be for example about 10 to 274 turns-to-failure, which translates to about 6 to 168 turns-to-failure per inch of strand length assuming a 1⅝ inch strand length.

Based upon manufacturing experience, it is anticipated that if cold work above 65% or ultimate tensile strength levels above 250 kpsi are imparted, the torsional ductility will become independent of final anneal duration. This is thought to be the result of there being simply too much cold work to relax by annealing.

Figure 10:
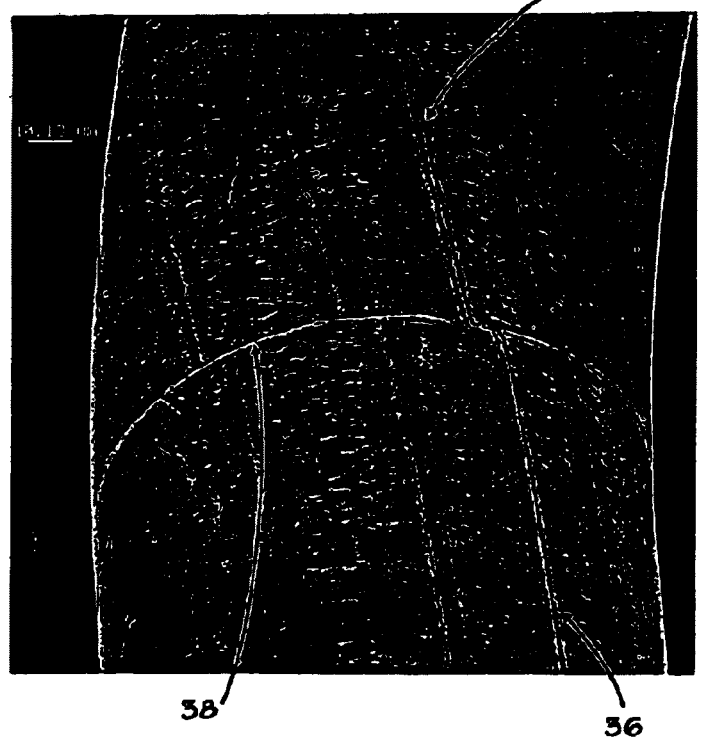
FIG. 10 is a scanning electron microscopy photograph of a conventionally produced wire viewed from the side and undergoing torsional deformation.
Figure 11:
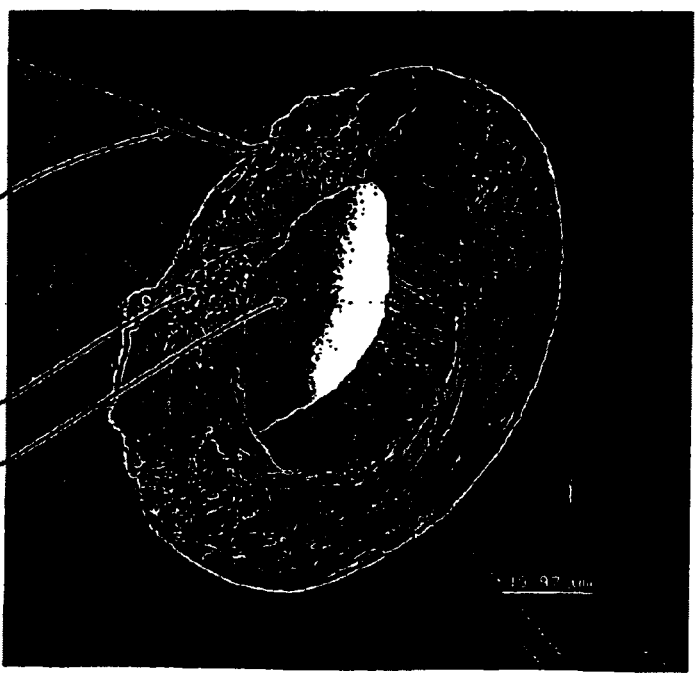
FIG. 11 is a scanning electron microscopy photograph of the wire depicted in FIG. 10 following torsional failure.
Figure 12:
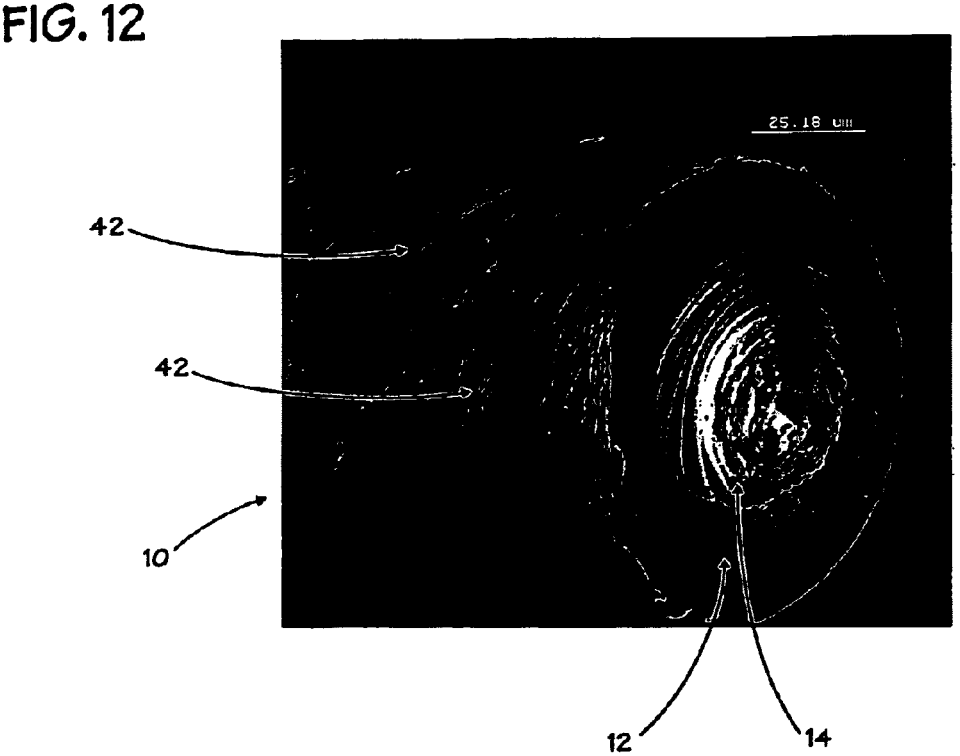
FIG. 12 is a scanning electron microscopy photograph of an exemplary embodiment of a wire fabricated in accordance with the present invention following torsional failure.

Dramatic visual evidence of the benefits of the present invention may be seen in FIGS. 10, 11 and 12. FIGS. 10 and 11 are scanning electron microscopy ("SEM") photographs of a conventionally fabricated MP35N silver clad wire 34 that was subjected to a short duration final anneal prior to final drawing. More specifically, FIG. 10 is a SEM photograph of the conventional wire 34 photographed from the side. A key in microns is provided for scale. The wire 34 in the photograph in FIG. 10 is undergoing torsion testing and has already begun plastic deformation. Striations 36 on the outer surface of the wire 34 either side of a fracture plane 38 exhibits some evidence of twisting. Due to the limited torsional ductility of the conventionally produced wire 34, most of the torsional strain is concentrated at the fracture plane 38. This highly localized concentration of torsional strain is clear evidence of the limited ability of the conventionally produced wire 34 to distribute torsional strain over a much larger surface area of the wire 34 that might otherwise translate into much higher torsional ductility. FIG. 11 is a SEM photograph of an end view of the wire 34 following torsional failure. The silver core 40 of the wire has been etched slightly to reveal the interior structure of the wire 34. The wire 34 fractured along the fracture plane 38 without significant additional twisting of the striations 36.

The limited ability of the conventional wire 34 to distribute the torsional strain as evidenced in the limited twisting of the striations 36 shown in FIGS. 10 and 11 should be contrasted with the wire 10 produced in accordance with the present invention depicted in FIG. 12. FIG. 12 shows the wire 10 after torsional failure. Thus, the ends of the tube 14 and the silver core 14 at the fracture plane are visible. In contrast to the conventionally produced wire 34 depicted in FIGS. 10 and 11, the striations 42 in the wire 10 in accordance with the present invention exhibit a significant twisting angle relative to the long axis of the wire 10. This is visible evidence of a much greater distribution of torsional strain in the wire 10 produced in accordance with the present invention, which is consistent with the much higher torsional ductility observed in the wire prior 10 to torsional failure.

Figure 13:
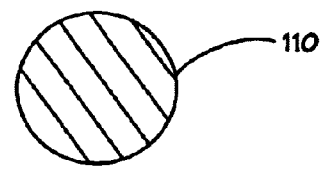
FIG. 13 is a cross-sectional view similar to FIG. 2, but depicting an alternate exemplary embodiment of a wire fabricated in accordance with the present invention.
Figure 14:
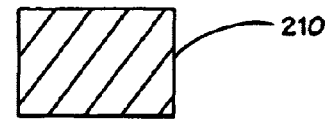
FIG. 14 is a cross-sectional view similar to FIG. 2, but depicting another alternate exemplary embodiment of a wire fabricated in accordance with the present invention.

The foregoing illustrative embodiments are depicted in the context of a clad wire, that is, a wire consisting of a tube and an internal core. However, the skilled artisan will appreciate that other wire configurations are envisioned in accordance with the present invention. For example, and as depicted in FIG. 13, a wire 110 may consist of a strand that does not include a core. The strand may be composed of the same materials used to fabricate the tube 12 described elsewhere herein. It is expected that the mechanical behavior of solid strands will closely track the behavior of clad wires, particularly for soft core materials. Additionally, other than circular cross-sections are envisioned. For example, and as depicted in FIG. 14, a wire 210 may be fabricated with a rectangular cross-section as shown. Furthermore, the use of other than a circular cross-section may be combined with either a clad or unclad wire as the case may be. These two shapes represent just a few of the myriad of possible wire cross-sections envisioned in accordance with the present invention.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents and alternatives falling within the spirit and scope of the invention as defined by the following appended claims.

What is claimed is:

1. A wire, comprising:
   a core; and
   a tube around the core, the tube being composed of an alloy containing about 33 to 37% nickel, about 31.5 to 39% cobalt, about 9 to 10.5% molybdenum, and about 19 to 21% chromium, the wire having an ultimate tensile strength of about 150 to 250 kpsi, an amount of cold work following a final anneal and a torsional ductility of greater than about 6 turns-to-failure per inch of the wire.

2. The wire of claim 1, wherein the amount of cold work comprises less than about 65%.

3. The wire of claim 1, wherein the amount of cold work comprises about 10 to 65%.

4. The wire of claim 1, wherein the core comprises silver.

5. The wire of claim 1, wherein the core comprises gold, tantalum or copper.

6. The wire of claim 1, wherein the wire has a total cross-sectional area, the core having a cross-sectional area that comprises about 10 to 45% of the total cross-sectional area.

7. A wire, comprising:
   a core; and
   a tube around the core, the tube being composed of MP35N, the wire having an ultimate tensile strength of about 150 to 250 kpsi, having an amount of cold work following final anneal and a torsional ductility greater than about 6 turns-to-failure per inch of the wire.

8. The wire of claim 7, wherein the core comprises silver.

9. The wire of claim 7, wherein the core comprises gold, tantalum or copper.

10. The wire of claim 7, wherein the wire has a total cross-sectional area, the core having a cross-sectional area that comprises about 10 to 45% of the total cross-sectional area.

11. A wire, comprising:
   a strand of alloy containing about 33 to 37% nickel, about 31.5 to 39% cobalt, about 9 to 10.5% molybdenum, and about 19 to 21% chromium, and having an ultimate tensile strength of about 150 to 250 kpsi, an amount of cold work following final anneal and a torsional of ductility greater than about 6 turns-to-failure per inch of strand.

12. The wire of claim 11, wherein the strand has a torsional ductility of about 6 to 168 turns-to-failure per inch of strand.

13. The wire of claim 11, wherein the amount of cold work comprises less than about 65%.

14. The wire of claim 11, wherein the amount of cold work comprises about 10 to 65%.

15. An electrical lead for a medical device, comprising:
an electrode;
an insulating sleeve coupled the electrode; and
a wire coupled to the electrode and at least partially positioned in the insulating sleeve, the wire having a core and a tube around the core, the tube being composed of an alloy containing about 33 to 37% nickel, about 31.5 to 39% cobalt, about 9 to 10.5% molybdenum, and about 19 to 21% chromium, the wire having an ultimate tensile strength of about 150 to 250 kpsi, an amount of cold work following a final anneal and a torsional ductility of greater than about 6 turns-to-failure per inch of the wire.

16. A wire, comprising:
a core; and
a tube around the core, the tube being composed of a material selected from the group consisting of (a) an alloy containing about 33 to 37% nickel, about 31.5 to 39% cobalt, about 9 to 10.5% molybdenum, and about 19 to 21% chromium, (b) Elgiloy, © L605, (d) Inconel and (e) austenitic stainless steels, the wire having an ultimate tensile strength of about 150 to 250 kpsi, having an amount of cold work following final anneal and a torsional ductility greater than about 6 turns-to-failure per inch of the wire.

17. The wire of claim 16, wherein the core comprises silver, gold, tantalum, copper or alloys of these.

* * * * *